United States Patent
Amos, Jr.

(10) Patent No.: US 8,246,690 B2
(45) Date of Patent: Aug. 21, 2012

(54) STENT WITH SOLUBLE BLADDER RETENTION MEMBER

(75) Inventor: Raymond G. Amos, Jr., Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 107 days.

(21) Appl. No.: 12/731,836

(22) Filed: Mar. 25, 2010

(65) Prior Publication Data

US 2010/0179666 A1    Jul. 15, 2010

Related U.S. Application Data

(63) Continuation of application No. 11/855,274, filed on Sep. 14, 2007, now Pat. No. 7,713,308.

(60) Provisional application No. 60/826,642, filed on Sep. 22, 2006.

(51) Int. Cl.
*A61F 2/04* (2006.01)
*A61M 5/00* (2006.01)

(52) U.S. Cl. .......... 623/23.66; 623/23.7; 604/8

(58) Field of Classification Search .......... 604/8–9; 623/23.64–23.7
See application file for complete search history.

(56) References Cited

U.S. PATENT DOCUMENTS

| | | |
|---|---|---|
| 3,999,551 A | 12/1976 | Spitz et al. |
| 4,212,304 A | 7/1980 | Finney |
| 4,334,327 A | 6/1982 | Lyman et al. |
| 4,512,770 A | 4/1985 | Cianci et al. |
| 4,574,806 A | 3/1986 | McCarthy |
| 4,685,905 A | 8/1987 | Jeanneret nee Aab |
| 4,820,262 A | 4/1989 | Finney |
| 4,931,037 A * | 6/1990 | Wetterman .......... 604/8 |
| 5,019,102 A | 5/1991 | Hoene |
| 5,049,138 A | 9/1991 | Chevalier et al. |
| 5,085,629 A | 2/1992 | Goldberg et al. |
| 5,120,317 A | 6/1992 | Luther |
| 5,205,830 A | 4/1993 | Dassa et al. |
| 5,401,257 A | 3/1995 | Chevalier, Jr. et al. |
| 5,464,450 A | 11/1995 | Buscemi et al. |

(Continued)

FOREIGN PATENT DOCUMENTS

DE    1250704 B    9/1967

(Continued)

OTHER PUBLICATIONS

Office Action for U.S. Appl. No. 11/842,410, mailed on Sep. 28, 2009, 13 pages.

(Continued)

*Primary Examiner* — Thomas J Sweet
*Assistant Examiner* — Andrew Iwamaye

(57) ABSTRACT

Ureteral stents having at least a portion of a proximal end of the ureteral stent constructed with a material that dissolves after being exposed to a bodily fluid for a period of time are disclosed herein. At least a portion of the proximal end portion of the elongate member includes a dissolving portion configured to dissolve in response to being exposed to a bodily fluid for a period of time. The elongate member also includes a non-dissolving portion that includes the entire retention member of the distal end portion and is substantially stable in the bodily fluid of the urinary tract of the patient. In some embodiments, a medial portion of the ureteral stent is also constructed with one or more dissolving materials. In some implementations, the proximal and/or the medial portions of the ureteral stent are constructed using various combinations of dissolving and non-dissolving materials.

19 Claims, 7 Drawing Sheets

U.S. PATENT DOCUMENTS

| | | | |
|---|---|---|---|
| 5,500,013 | A | 3/1996 | Buscemi et al. |
| 5,599,291 | A | 2/1997 | Balbierz et al. |
| 5,814,006 | A | 9/1998 | Planz |
| 5,964,744 | A | 10/1999 | Balbierz et al. |
| 6,160,084 | A | 12/2000 | Langer et al. |
| 6,228,111 | B1 | 5/2001 | Tormala et al. |
| 6,284,333 | B1 | 9/2001 | Wang et al. |
| 6,368,356 | B1 | 4/2002 | Zhong et al. |
| 6,387,124 | B1 | 5/2002 | Buscemi et al. |
| 6,620,202 | B2 | 9/2003 | Bottcher et al. |
| 6,676,624 | B2 | 1/2004 | Gellman |
| 6,709,465 | B2 | 3/2004 | Mitchell et al. |
| 6,719,804 | B2 * | 4/2004 | St. Pierre .................. 623/23.7 |
| 6,887,215 | B2 | 5/2005 | McWeeney |
| 6,908,447 | B2 | 6/2005 | McWeeney et al. |
| 6,913,765 | B2 | 7/2005 | Li et al. |
| 7,291,180 | B2 * | 11/2007 | St. Pierre .................. 623/23.66 |
| 7,713,308 | B2 | 5/2010 | Amos, Jr. |
| 7,951,206 | B2 * | 5/2011 | St. Pierre .................. 623/23.66 |
| 7,993,411 | B2 * | 8/2011 | Kennedy et al. ............ 623/23.7 |
| 2003/0074082 | A1 | 4/2003 | Bottcher et al. |
| 2003/0153972 | A1 | 8/2003 | Helmus |
| 2003/0199993 | A1 | 10/2003 | Gellman et al. |
| 2004/0015187 | A1 | 1/2004 | Lendlein et al. |
| 2004/0143209 | A1 | 7/2004 | Liu et al. |
| 2004/0249441 | A1 | 12/2004 | Miller et al. |
| 2005/0043783 | A1 | 2/2005 | Amis et al. |
| 2005/0085916 | A1 | 4/2005 | Li et al. |
| 2005/0209680 | A1 | 9/2005 | Gale et al. |
| 2005/0228481 | A1 | 10/2005 | Manasas et al. |
| 2006/0025726 | A1 * | 2/2006 | Fischer et al. ................ 604/265 |
| 2008/0086215 | A1 * | 4/2008 | St. Pierre .................. 623/23.66 |
| 2011/0196507 | A1 * | 8/2011 | St. Pierre .................. 623/23.66 |

FOREIGN PATENT DOCUMENTS

| | | |
|---|---|---|
| DE | 3339179 A1 | 5/1985 |
| DE | 8614013 U1 | 8/1986 |
| EP | 0208841 A2 | 1/1987 |
| FR | 2133083 A5 | 11/1972 |
| FR | 2409747 A1 | 6/1979 |
| WO | 80/01507 A1 | 7/1980 |
| WO | 89/05127 A1 | 6/1989 |
| WO | 94/25093 A1 | 11/1994 |
| WO | 96/11721 A1 | 4/1996 |

OTHER PUBLICATIONS

Office Action for U.S. Appl. No. 11/842,410, mailed on Mar. 24, 2009, 17 pages.

International Search Report and Written Opinion for PCT Application No. PCT/US2007/076640, mailed on Nov. 12, 2007, 5 pages.

Hercules Incorporated "KLUCEL—Physical and Chemical Properties", Aqualon Division, 2001, 26 pages.

Dupont Company, "DuPont™ Elvax, EVA resins for Molding, Compounding, and Extrusion", online] [retrieved on Sep. 9, 2005] Retrieved from the Internet <URL:http://www.dupont.com/indistrial-polymers/elvax/H-08772-2/H-08772-2.html >, 7 pages.

Boston Scientific, "Polaris™ Ureteral Stent, Ureteral Stent—Firm Placement, Soft Comfort, Boston Scientific", [online] [retrieved on Aug. 29, 2005] Retrieved from the Internet, < URL: http://www.bostonscientific.com/med_specality/deviceDetail.jsp?task=tskBasicDevice.js p... >, 1 page.

Hercules Incorporated, "Klucel® Hydroxypropylcellulose (HPC)", 2004, 3 pages.

International Search Report and Written Opinion for PCT Application No. PCT/US2007/078849, mailed on Jan. 22, 2008.

"International Search Report for PCT Application No. PCT/US1994/004526, mailed on Aug. 3, 1994", 1 page.

International Search Report for Application No. PCT/EP1988/001113, mailed on Mar. 29, 1989, 8 pages.

International Search Report for Application No. PCT/US1995/012826, mailed on Jan. 31, 1996, 1 page.

* cited by examiner

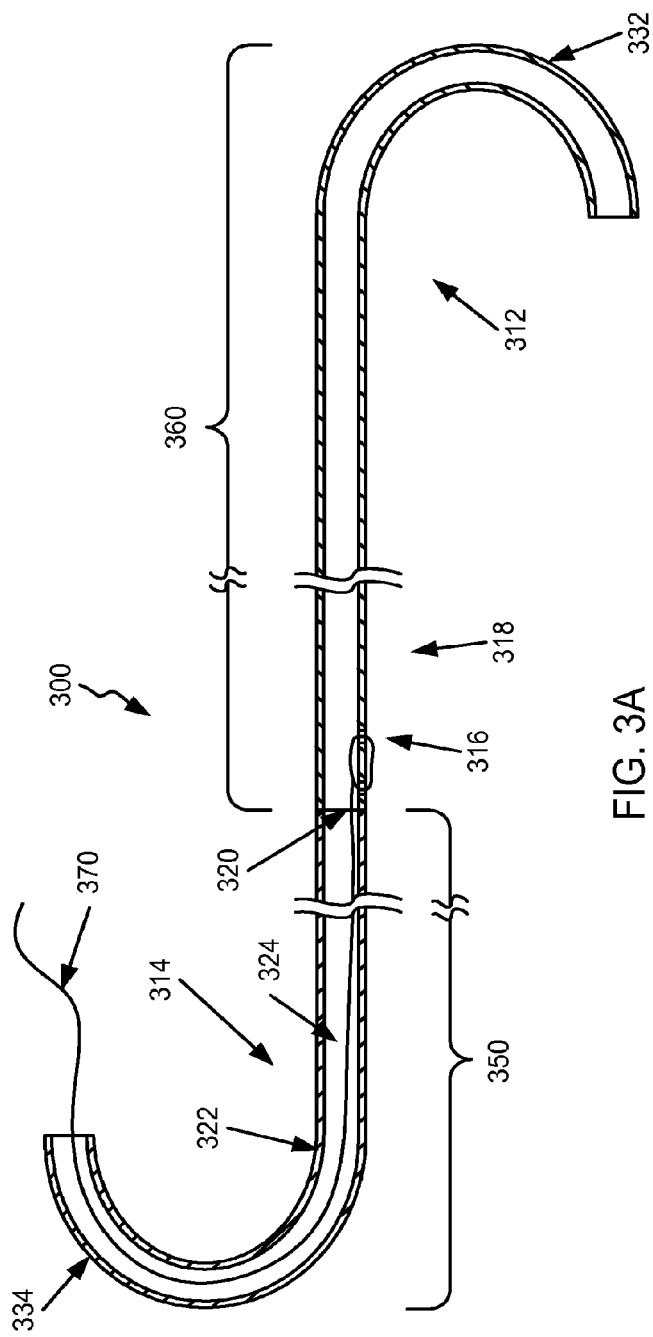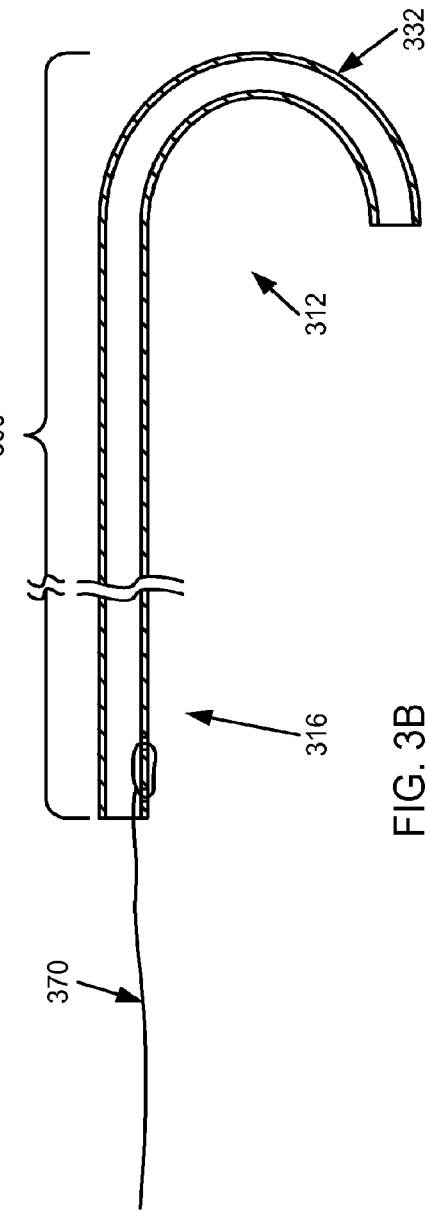
FIG. 3A
FIG. 3B

STENT WITH SOLUBLE BLADDER RETENTION MEMBER

CROSS REFERENCE TO RELATED APPLICATIONS

This application is a continuation of U.S. patent application Ser. No. 11/855,274, now U.S. Pat. No. 7,713,308 filed Sep. 14, 2007, entitled "STENT WITH SOLUBLE BLADDER RETENTION MEMBER," which, in turn, claims priority to U.S. patent application Ser. No. 60/826,642, filed Sep. 22, 2006, entitled "STENT WITH SOLUBLE BLADDER RETENTION MEMBER", both of which are incorporated by reference herein in their entirety.

BACKGROUND

The disclosed invention relates generally to a medical device, and in particular, to a ureteral stent with a dissolving portion.

Known ureteral stents are typically placed within a urinary tract of a patient such that one end portion of the ureteral stent is located in a kidney of the patient and another end portion of the ureteral stent is located in either a bladder or a ureter of the patient. Known ureteral stents are typically positioned within the urinary tract of the patient by placing a guidewire within the patient, sliding the ureteral stent on the guidewire, and then forcing the ureteral stent along the guidewire into a desired position within the patient using a push rod. Such ureteral stents are often removed from the patient by pulling the ureteral stent from the urinary tract of the patient.

Some known ureteral stents include a retention member at a kidney end portion of the ureteral stent and a retention member at a bladder end portion of the ureteral stent. The retention member of the bladder end portion of the ureteral stent is configured to be placed within the bladder to help prevent migration of the ureteral stent upwardly toward the kidney. Similarly, the retention member of the kidney end portion is configured to be placed within the kidney to help prevent migration of the ureteral stent downwardly toward the bladder.

Known ureteral stents often cause pain and discomfort to the patient once the ureteral stents are positioned within the body. In particular, the retention member of the bladder end portion can irritate sensitive regions in the bladder such as the trigone region and/or intramural tunnel. Thus, a need exists for a ureteral stent that substantially reduces and/or minimizes irritation of sensitive regions of a urinary tract of a patient.

SUMMARY

A ureteral stent includes an elongate member that is configured to be disposed within a urinary tract of a patient to convey urine from a first portion of the urinary tract of the patient to a second portion of the urinary tract of the patient. The elongate member has a distal end portion, a proximal end portion, and a medial portion disposed between the distal end portion and the proximal end portion. The distal end portion includes a retention member configured to help retain at least a portion of the elongate member within a kidney of the patient and the proximal end portion includes a retention member configured to help retain at least a portion of the elongate member within a bladder of the patient.

In some embodiments, the proximal end portion of the elongate member includes a dissolving portion configured to dissolve in response to being exposed to a bodily fluid for a period of time. The elongate member also has a non-dissolving portion that includes the entire retention member of the distal end portion and is substantially stable in the bodily fluid of the urinary tract of the patient.

In another embodiment, the retention member of the distal end portion is constructed of a stent material that is substantially stable in the bodily fluid of the urinary tract of the patient. The proximal end portion includes a dissolving portion that is configured to dissolve in response to being exposed to a bodily fluid for a period of time and a non-dissolving portion that is substantially stable in the bodily fluid of the urinary tract of the patient.

BRIEF DESCRIPTION OF THE DRAWINGS

The present invention is described with reference to the accompanying drawings. In the drawings, identical or like reference numbers indicate identical or functionally similar elements.

FIG. 3A is a schematic diagram of a side cross-sectional view of a ureteral stent, according to an embodiment of the invention, before a dissolving portion dissolves.

FIG. 3B is a schematic diagram of a side cross-sectional view of the ureteral stent of FIG. 3A after the dissolving portion has dissolved.

DETAILED DESCRIPTION

Ureteral stents having at least a portion of the ureteral stent constructed of a material that dissolves (e.g., soluble) after being exposed to a bodily fluid for a period of time are disclosed herein. Specifically, in one embodiment, the proximal end portion is configured to dissolve to substantially reduce and/or minimize irritation of sensitive regions in a bladder of a patient after the ureteral stent has been inserted. A distal end of the ureteral stent, in contrast, is constructed of a material that is formulated to be substantially stable in the bodily fluid of the patient. In some embodiments, at least a portion of a medial portion of the ureteral stent is also constructed with one or more dissolving materials. In other embodiments, the proximal portion and/or the medial portion of the ureteral stent are constructed using various combinations of dissolving and/or non-dissolving materials.

Figure 1:
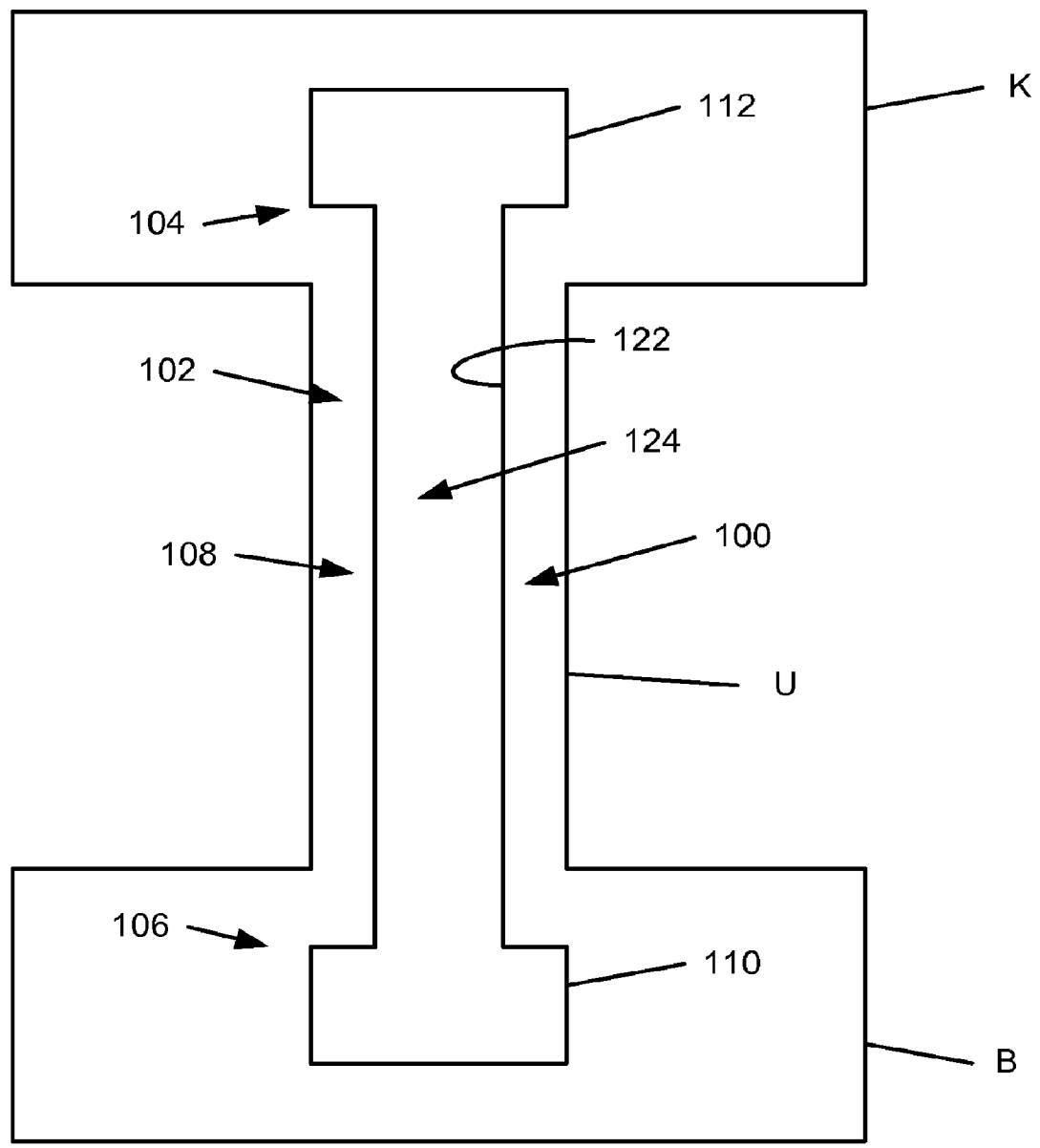
FIG. 1 is a schematic diagram that illustrates a ureteral stent, according to an embodiment of the invention, disposed within a urinary tract of a patient.

FIG. 1 is a schematic diagram that illustrates a ureteral stent 100, according to an embodiment of the invention, disposed within a urinary tract of a patient. The ureteral stent 100 is positioned within a patient such that it extends from the kidney K, through the ureter U, and to the bladder B. The ureteral stent 100 is configured to facilitate the movement of fluid within a urinary tract of a patient, for example, from the kidney K to the bladder B via the ureter U.

The ureteral stent 100 includes an elongate member 102 having a distal end portion 104, a proximal end portion 106, and a medial portion 108 extending between the distal end portion 104 and the proximal end portion 106. The proximal end portion 106 includes a retention member 110. Similarly, the distal end portion 104 includes a retention member 112.

The retention member 110 of the proximal end portion 106 of the ureteral stent 100 is configured to be placed within the bladder B to help prevent migration of the ureteral stent 100 upwardly toward the kidney K. Similarly, the retention member 112 of the distal end portion 104 is configured to be placed within the kidney K to help prevent migration of the ureteral stent 100 downwardly toward the bladder B. Accordingly, the retention members 110 and 112 are configured to help retain the ureteral stent 100 in place within the urinary tract of the patient. The retention members 110 and 112 may be configured in a variety of different shapes and sizes, such as a loop, a J hook, a pig tail, a planar coil, and/or a malecot.

The ureteral stent 100 includes a side wall 122. In one embodiment the side wall 122 defines a lumen 124. The lumen 124 extends from the distal end portion 104 to the proximal end portion 106 of the ureteral stent 100. In some embodiments, the lumen 124 only extends through a portion of the ureteral stent 100. In other embodiments, the ureteral stent 100 does not include a side wall 122 that defines a lumen 124.

At least a portion of the proximal end portion 106 of the ureteral stent 100, and in some embodiments a portion of the medial portion 108, are constructed of at least one dissolving material that is formulated to dissolve (e.g., soluble) in a bodily fluid after being inserted into the urinary tract of the patient. The dissolving material is configured to dissolve in a bodily fluid such as water, urine, mucous, etc. within hours such as within forty-eight hours) of being placed in a specified location. After the dissolving of the proximal end portion 106 and/or the medial portion 108 have dissolved in the bodily fluid, the mixture of the bodily fluid and the dissolved and/or partially dissolved materials separated from the ureteral stent 100 can be voided from the bladder B of the patient. The dissolving material can be, for example, klucel (Hydroxypropylcellulose) or a different material configured to have, for example, a specified dissolution rate, length, biocompatibility, and/or level of rigidity.

The proximal end portion 106 (including the retention member 110) is configured to dissolve so that the proximal end portion 106 does not irritate sensitive regions within the bladder B (e.g., trigone region). Because the tendency for the ureteral stent 100 to migrate antegrade or upwards into the kidney K is low compared with the tendency towards downward or retrograde migration into the bladder B due to gravity and downward peristalsis in the ureter, dissolution of the proximal end portion 106 after placement of the ureteral stent 100 can be beneficial. In other words, irritation of sensitive regions within the bladder B by the ureteral stent 100 and risk of undesirable movement of the ureteral stent 100 can be simultaneously reduced and/or minimized.

The ureteral stent 100 also includes a non-dissolving portion. Specifically, the distal end portion 104 of the ureteral stent 100, in contrast to the proximal end portion 106, is constructed of a stent material that is substantially stable in a bodily fluid of the patient (also can be referred to as non-dissolving). The non-dissolving portion of the ureteral stent 100 remains in the patient until the ureteral stent 100 is removed using a known or conventional ureteral stent extraction technique (e.g., removal using a tether). In some embodiments, a portion of the medial portion 108, in addition to the distal end portion 104, is constructed of a non-dissolving material. The non-dissolving material can be, for example, a polyolefin or a polyurethane.

Figure 2:
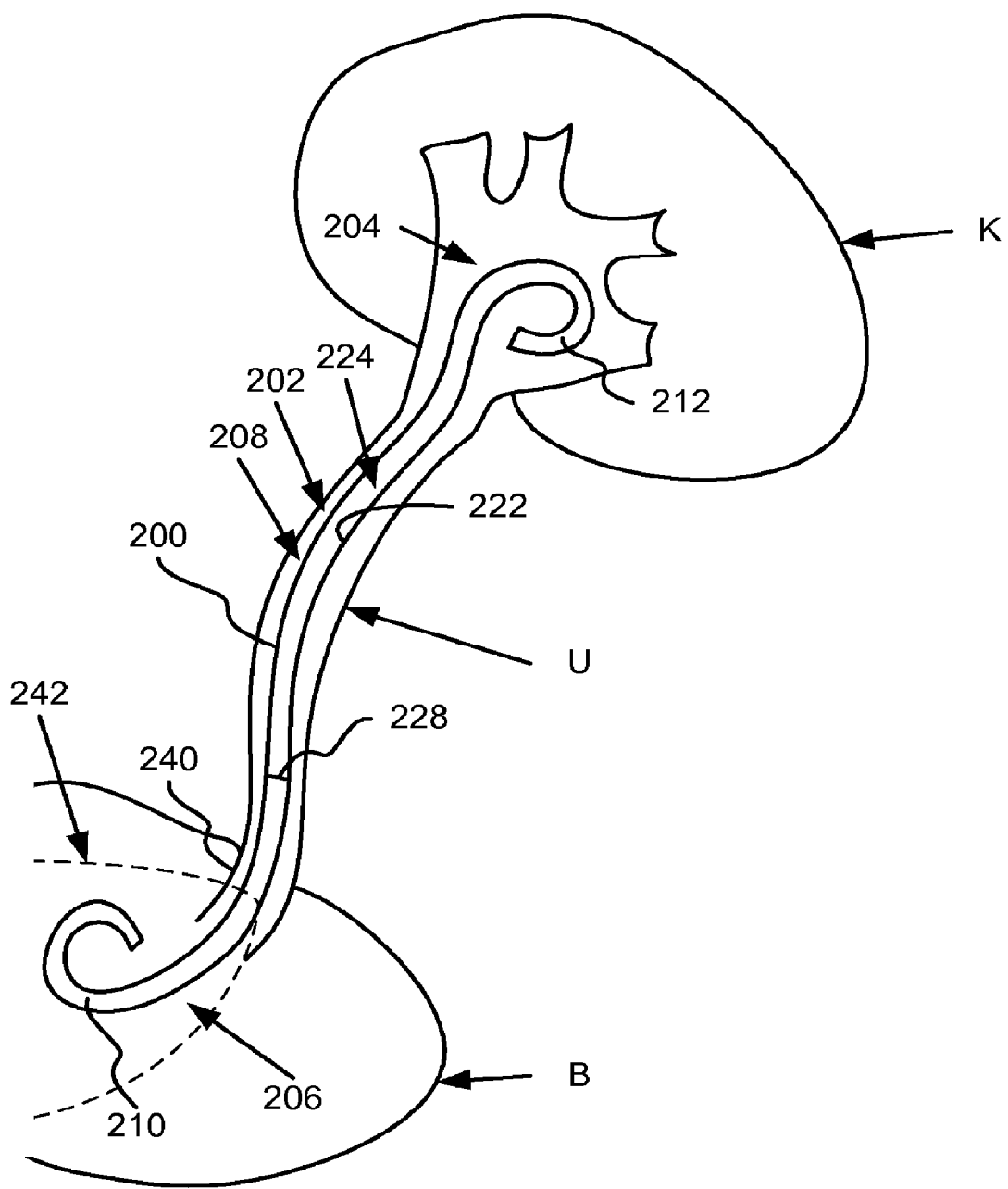
FIG. 2 is a schematic diagram of a side view of a ureteral stent, according to an embodiment of the invention, disposed within a urinary tract of a patient.

FIG. 2 is a schematic diagram of a side view of a ureteral stent, according to an embodiment of the invention, disposed within a urinary tract of a patient. The ureteral stent 200 includes an elongate member 202 having a distal end portion 204, a proximal end portion 206, and a medial portion 208 extending between the distal end portion 204 and the proximal end portion 206. The proximal end portion 206 includes a retention member 210. Similarly, the distal end portion 204 includes a retention member 212. The elongate member 202 of the ureteral stent 200 also includes a side wall 222 that defines a lumen 224 extending from the distal end portion 204 to the proximal end portion 206 of the ureteral stent 200. The ureteral stent 200 is positioned within a patient such that it extends from a kidney K, through a ureter U, and into a trigone region 242 of a bladder B through an intramural tunnel 240. The trigone region 242 is a smooth triangular region within the bladder B formed by the intramural tunnel 240, a second intramural tunnel (not shown), and the internal urethral orifice (not shown).

At least a portion of the proximal end portion 206, and in some embodiments a portion of the medial portion 208, is formulated to dissolve in a bodily fluid after being inserted into a patient. The distal end portion 204, and, in some embodiments, a portion of the medial portion 208, is formed of a non-dissolving material that is substantially stable in the bodily fluid. In the illustrated embodiment, a distinct separation of the non-dissolving portion and the dissolving portion of the ureteral stent 200 is shown at 228.

The dissolving portion of the proximal end portion 206 can be sized so that irritation of the trigone region 242 and/or intramural tunnel 240 can be substantially reduced and/or minimized. For example, the ureteral stent 200 can be configured so that after the dissolving portion of the proximal end portion 206 dissolves, the remaining portion of the ureteral stent 200 does not extend into the trigone region 242 or even into the intramural tunnel 240. In some embodiments, the ureteral stent is configured so that up to approximately one-third of the overall length of the ureteral stent dissolves. In some embodiments, the ureteral stent can be configured so that more than approximately one-third of the overall length of the ureteral stent dissolves.

The rate of dissolution of the dissolving portion of the proximal end portion 206 can vary depending upon the type of material used as the dissolving portion and/or the geometry of the ureteral stent 200. For example, portions of the dissolving portion of the proximal end portion 206 can be configured to facilitate dissolution (e.g., porously configured structures, thin portions). After the dissolving portion of the proximal end portion 206 has dissolved in bodily fluids, the mixture of bodily fluids and the dissolved material from the ureteral stent 200 can be voided from the bladder B of the patient. Partially dissolved portions of the proximal end portion 206 that have been dissolved away and/or separated from the ureteral stent 200, in some embodiments, can also be naturally voided from the bladder B of the patient.

FIGS. 3A and 3B are schematic diagrams of side cross-sectional views of a ureteral stent 300 at two different times. The difference(s) in FIGS. 3A and 3B illustrate a temporal change in the structure of the ureteral stent 300 as a result of the dissolution of a dissolving portion 350 of the ureteral stent 300. FIG. 3A is a schematic diagram of a side cross-sectional view of the ureteral stent 300 before the dissolving portion 350 has dissolved. FIG. 3B is a schematic diagram of a side cross-sectional view of the ureteral stent of FIG. 3A after the dissolving portion 350 has dissolved, leaving a non-dissolving portion 360.

The ureteral stent 300 includes an elongate member 318 having a distal end portion 312, a proximal end portion 314, and a medial portion 316 extending between the distal end portion 312 and the proximal end portion 314. The ureteral stent 300 also includes a side wall 322 that defines a lumen 324 extending from the distal end portion 314 to the proximal end portion 312 of the ureteral stent 300. The proximal end portion 314 includes a retention member 334 and the distal end portion 312 includes a retention member 332. In this embodiment, a distinct separation of the dissolving portion 350 and the non-dissolving portion 360 of the ureteral stent 300 is shown at 320. Although the separation at 320 is shown as a straight line in this embodiment, in some embodiments, the non-dissolving portion 360 and dissolving portion 350 can overlap, meet in an interlocking fashion, and so forth. The ureteral stent 300 also includes a tether 370 that can be used for removing the non-dissolving portion 360 of the ureteral stent 300.

FIG. 3B illustrates the non-dissolving portion 360 of the ureteral stent 300 that remains after the dissolving portion 350 of the ureteral stent 300 has dissolved. Specifically, as best illustrated in FIG. 3B, the entire retention member 332 of the distal end portion 312 is formulated with the non-dissolving material. The dissolving portion 350 can be configured to dissolve within hours of being inserted into a patient. In other embodiments, the dissolving portion is configured to dissolve in more or less time. In some embodiments, the dissolving portion 350 dissolves slowly over a longer period of time.

Figure 4:
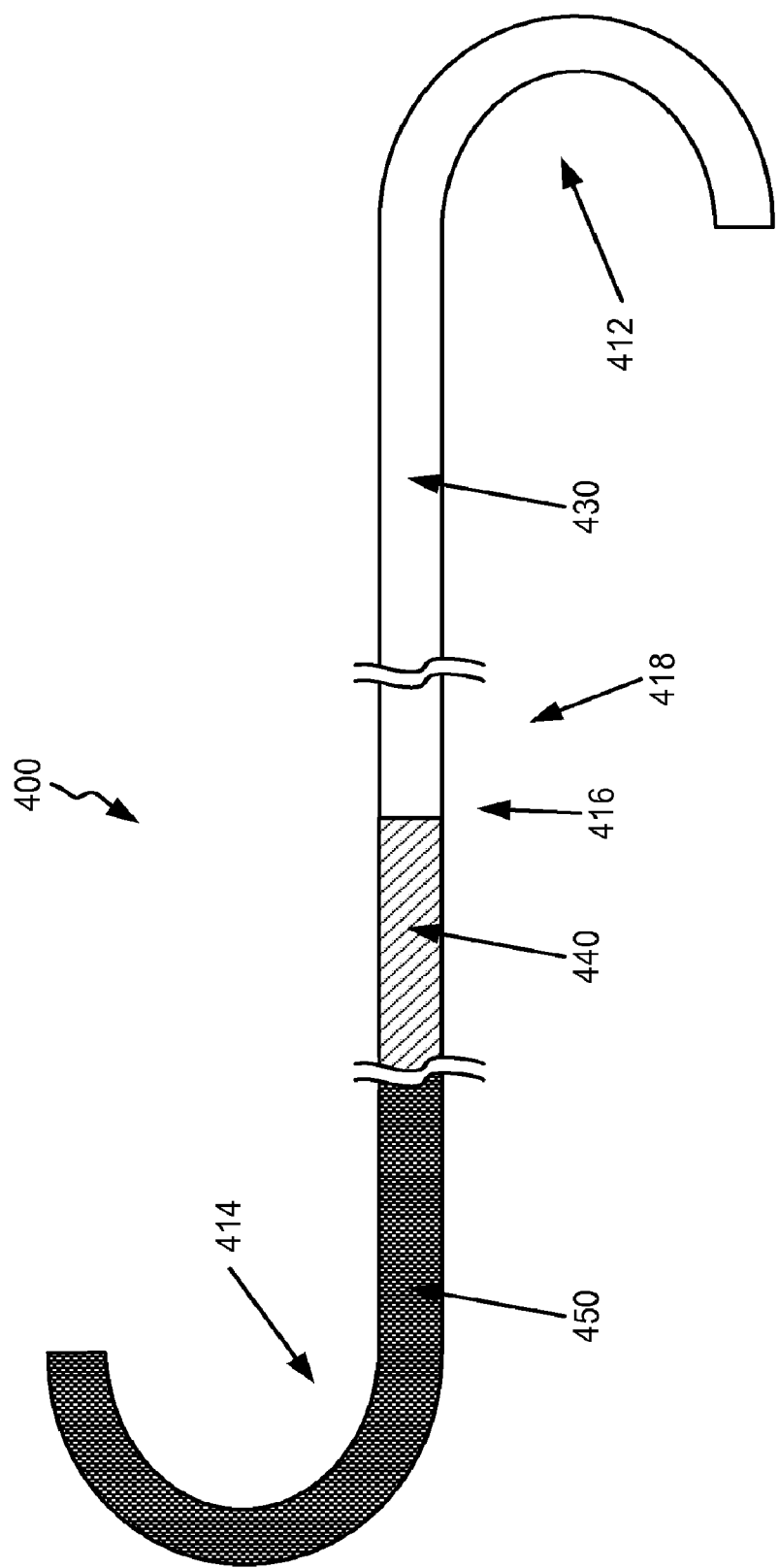
FIG. 4 is a schematic diagram of a side view of a ureteral stent, according to an embodiment of the invention.

FIG. 4 is a schematic diagram of a side view of a ureteral stent 400, according to an embodiment of the invention, that includes an elongate member 418 having a distal end portion 412, a proximal end portion 414, and a medial portion 416. In this embodiment, the distal end portion 412 is formulated with a non-dissolving material 430, the proximal end portion 412 is formulated with a first dissolving material 440, and the medial portion 416 is formulated with a second dissolving material 450. The first dissolving material 440 and the second dissolving material 450 can be configured to have any combination of, for example, dissolution rates, lengths, biocompatibility, and/or levels of rigidity. In some embodiments, the ureteral stent 400 is constructed with multiple types of dissolving and/or non-dissolving materials.

Figure 5:
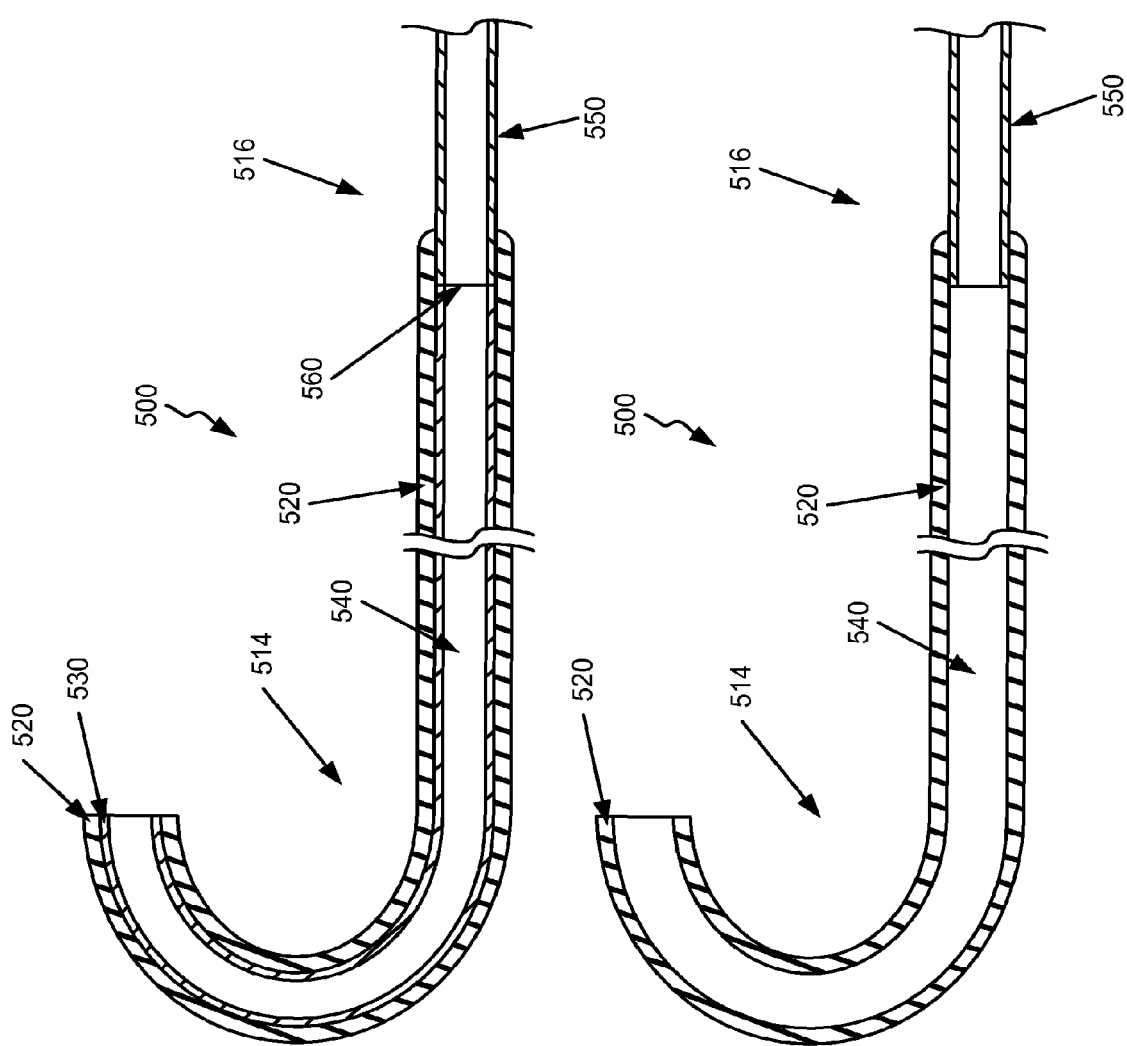
FIG. 5A is a schematic diagram of a side cross-sectional view of a ureteral stent, according to an embodiment of the invention, before a dissolving material dissolves.
FIG. 5B is a schematic diagram of a side cross-sectional view of the ureteral stent of FIG. 5A after the dissolving material has dissolved.

FIGS. 5A and 5B are schematic diagrams of side cross-sectional views of a ureteral stent 500 at two different times. The difference(s) between FIGS. 5A and 5B illustrate a temporal change in the structure of the ureteral stent 500 as a result of the dissolution of a portion of the ureteral stent 500. The ureteral stent 500 is configured with a soft non-dissolving material 520 (e.g., ultra-soft), a dissolving material 530, and a non-dissolving material 550. The dissolving material 530 and the non-dissolving material 550 are relatively rigid compared with the soft non-dissolving material 520. FIG. 5A is a side cross-sectional view of the ureteral stent 500 before the dissolving material 530 has dissolved. FIG. 5B is a side cross-sectional view of the ureteral stent 500 of FIG. 5A after the dissolving material 530 has dissolved.

The ureteral stent 500 shown in FIGS. 5A and 5B is configured such that the ureteral stent 500 is relatively rigid when being inserted into a urinary tract of a patient to facilitate placement of the ureteral stent 500. The ureteral stent 500 is also configured so that after being exposed for a period of time, the relatively rigid dissolving material 530 dissolves, leaving the soft non-dissolving material 520 (rather than the relatively rigid material) in sensitive areas within the urinary tract of the patient (e.g., intramural tunnel, trigone region). Patient comfort can be increased by substantially reducing and/or minimizing exposure of the sensitive areas within the urinary tract of the patient to the relatively rigid materials of the ureteral stent 500 (e.g., through dissolution) that facilitate placement.

FIGS. 5A and 5B show a proximal end portion 514 and a medial portion 516 of the ureteral stent 500. The ureteral stent 500 also includes a distal end portion that is not shown in FIG. 5A or 5B. Specifically, as illustrated in FIG. 5A, the proximal end portion 514 and a portion of the medial portion 516 of the ureteral stent 500 are constructed with the dissolving material 530 that is interior to the soft nondissolving material 520 (e.g., a soft and/or non-expanding material that is substantially stable in a urinary tract of a patient). A portion of the medial portion 516 is constructed of the non-dissolving material 550 that is relatively rigid compared with the soft nondissolving material 520. The dissolving material 530 and the non-dissolving material 530 meet at 560 and form side walls that define a lumen 540. In addition to being coupled with the dissolving material 530, the soft non-dissolving material 520 is coupled with the non-dissolving material 550 as shown in FIGS. 5A and 5B.

FIG. 5B is a schematic diagram that illustrates the soft non-dissolving material 520 and the non-dissolving material 550 after the dissolving material 530 has dissolved in response to being exposed to a bodily fluid of a patient for a period of the time. The lumen 540, after the dissolution of the dissolving material 530, is defined by the soft non-dissolving material 520 and the non-dissolving material 550. The ureteral stent 500 is configured so that when the dissolving material 530 dissolves and the ureteral stent 500 is in place within the patient, only the soft non-dissolving material 520 can come in contact with the most sensitive areas within the urinary tract of the patient such as the trigone region and/or intramural tunnel.

Although FIG. 5A shows that the soft non-dissolving material 520 and the dissolving material 530 are coextensive, in some embodiments, the two materials 520 and 530 are not coextensive (e.g., different lengths). In some embodiments, the portions of the ureteral stent 500 that are configured with the soft non-dissolving material 520, the dissolving material 530, and the non-dissolving material 550 can vary. For example in some embodiments, only a retention member portion of the proximal end portion 514 can be formulated with the soft non-dissolving material 520 and the dissolving material 530. In other embodiments, portions or all of the soft non-dissolving material 520, rather than being exterior to the dissolving material 530, can be interior to the dissolving material 530. In these scenarios, the soft non-dissolving material 520 can be coupled to the non-dissolving material 550 in a variety of configurations (e.g., on an interior portion of the non-dissolving material 550).

Also, in some embodiments, the ureteral stent 500 can be formulated with multiple types and/or combinations of soft and/or rigid materials that are nondissolving and/or dissolving. For example, rather than using a soft non-dissolving material, the proximal end portion 514 and/or a portion of the medial portion 516 can be formulated with a soft dissolving material that dissolves at a slower rate than the dissolving material.

Figure 6:
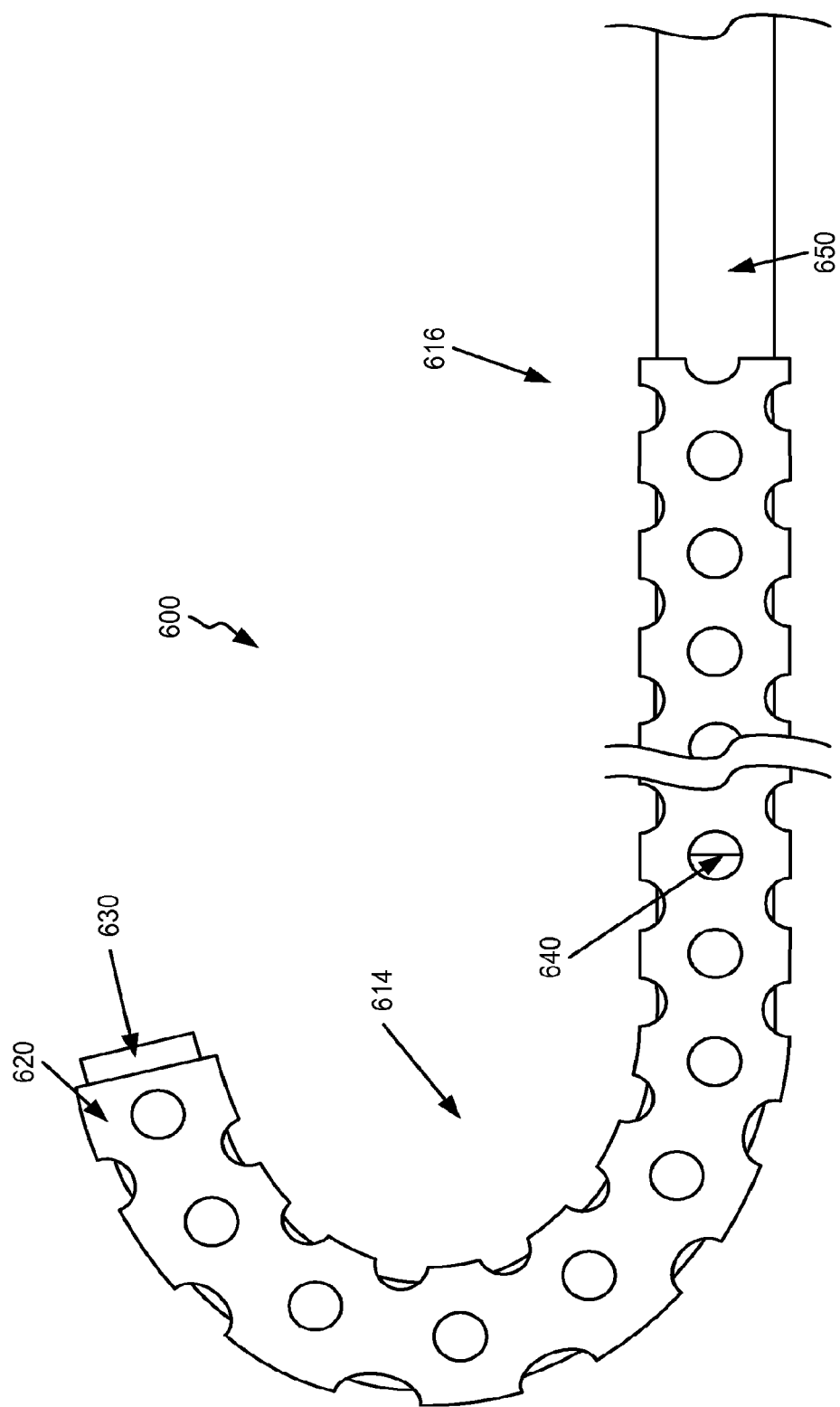
FIG. 6 is a schematic diagram of a side view of a proximal end portion and a medial portion of a ureteral stent, according to an embodiment of the invention.

FIG. 6 is a schematic diagram of a side view of a proximal end portion 614 and a medial portion 616 of a ureteral stent 600 that is formulated with an ultra-soft non-dissolving material 620 that is exterior to a rigid dissolving material 630, according to an embodiment of the invention. The medial portion 616 is formulated with a nondissolving material 650 that is rigid compared with the ultra-soft non-dissolving material 620. FIG. 6 illustrates the dissolving material 630 and the non-dissolving material 650 meet at 640. In this embodiment, the ultra-soft non-dissolving material 620 is perforated to promote the dissolution of the dissolving material 630 after the ureteral stent 600 is exposed to a bodily fluid within a urinary tract of a patient. As illustrated in FIG. 6, the perforations of the non-dissolving portion 620 are configured to convey fluid from a location outside of the lumen defined by the ureteral stent 600 to a location within the lumen defined by the ureteral stent 600 only after the dissolution of the dissolving material 630. Although in this embodiment, the ultra-soft non-dissolving material 620 is perforated with circles, the type of perforation can vary (e.g., squares, different sizes of circles, different patterns, etc.). In some embodiments, the dissolving material 630 and/or nondissolving material 650 are also perforated. In some embodiments, only the dissolving material 630 is perforated.

Figure 7:
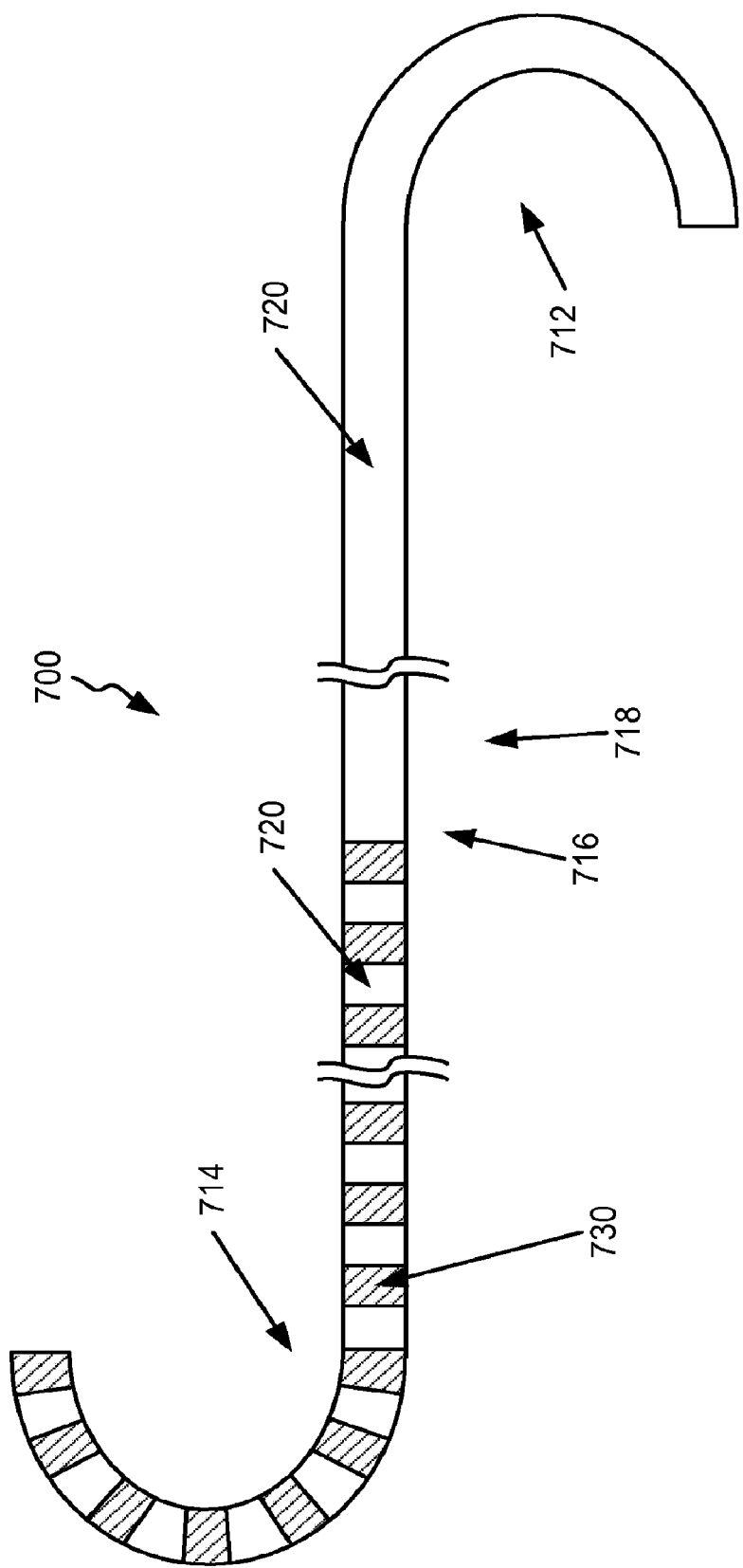
FIG. 7 is a schematic diagram of a side view of a ureteral stent, according to an embodiment of the invention.

FIG. 7 is a schematic diagram of a side view of a ureteral stent 700 that includes an elongate member 718 that has a distal end portion 712, a proximal end portion 714, and a medial portion 716, according to an embodiment of the invention. The distal end portion 712 is formulated with a non-dissolving material 720. The proximal end portion 714 and a portion of the medial portion 716 are formulated with small sections of alternating non-dissolving 720 and dissolving 730 materials. In some embodiments, the sections can be various shapes, patterns, and/or sizes. For example, the non-dissolving 720 and dissolving 730 can be configured in an interlocking fashion.

After the ureteral stent 700 is placed into a patient, the dissolving material 730 dissolves and leaves the distal end portion 712 that is constructed of a nondissolving material 720. Also, after the dissolving material 730 dissolves, the small sections of non-dissolving material 720 that are separated from the ureteral stent 700 can be voided from the patient. The non-dissolving portions 720 can be sized appropriately for voiding. In some embodiments, multiple types of dissolving material are used as the dissolving material 730. For example, a dissolving portion can be formulated with a first type of dissolving material and another dissolving portion can be formulated using a second type of dissolving material.

In conclusion, the present invention provides a ureteral stent having at least a portion of a proximal end of the ureteral stent constructed with a material that dissolves after being exposed to a bodily fluid for a period of time. Those skilled in the art can readily recognize that numerous variations and substitutions may be made in the invention, its use and its configuration to achieve substantially the same results as achieved by the embodiments described herein. Many variations, modifications and alternative constructions fall within the scope and spirit of the disclosed invention as expressed in the claims.

What is claimed is:

1. A ureteral stent, comprising:
an elongate member configured to be disposed within a urinary tract of a patient, the elongate member defining a lumen configured to convey urine from a first portion of the urinary tract of the patient to a second portion of the urinary tract of the patient, the elongate member having a distal end portion, a proximal end portion, and a medial portion disposed between the distal end portion and the proximal end portion,
the distal end portion including a retention member configured to help retain at least a portion of the elongate member within a kidney of the patient, the distal end portion being formed of a non-dissolving material and being devoid of a dissolving material, the proximal end portion including a retention member configured to help retain at least a portion of the elongate member within a bladder of the patient,
the proximal end portion including a dissolving portion and a non-dissolving portion, the non-dissolving portion having a plurality of pores, the dissolving portion being disposed within the non-dissolving portion and being configured to dissolve in response to being exposed to a bodily fluid for a period of time, the non-dissolving portion being substantially stable in the bodily fluid, the pores of the non-dissolving portion being configured to convey fluid from a location outside of the lumen defined by the elongate member to a location within the lumen defined by the elongate member only after the period of time.

2. The ureteral stent of claim 1, wherein at least a portion of the medial portion is constructed of a material that is substantially stable in the bodily fluid of the urinary tract of the patient, the non-dissolving portion of the proximal end portion is coupled to the material that is substantially stable in the bodily fluid of the urinary tract of the patient.

3. The ureteral stent of claim 1, wherein at least a portion of the medial portion is constructed of a material that is substantially stable in the bodily fluid of the urinary tract of the patient.

4. The ureteral stent of claim 1, wherein at least one of the dissolving portion and the non-dissolving portion includes at least a portion of the medial portion of the elongate member.

5. The ureteral stent of claim 1, wherein the non-dissolving portion is sized to minimize irritation of an intramural tunnel of the patient when the dissolving portion of the elongate member has dissolved.

6. The ureteral stent of claim 1, wherein the dissolving portion is constructed of a firm material compared with a material used to construct the non-dissolving portion.

7. The ureteral stent of claim 1, wherein the dissolving portion of the elongate member dissolves within forty-eight hours of the ureteral stent being placed in the urinary tract of the patient.

8. The ureteral stent of claim 1, wherein the dissolving portion includes at least two materials that dissolve at different rates.

9. The ureteral stent of claim 1, wherein the non-dissolving portion of the proximal end portione has a portion that overlaps at least a portion of the medial portion.

10. The ureteral stent of claim 1, wherein the non-dissolving portion has an outer diameter greater than the outer diameter of the medial portion.

11. A ureteral stent, comprising:
an elongate member configured to be disposed within a urinary tract of a patient, the elongate member defining a lumen configured to convey urine from a first portion of the urinary tract of the patient to a second portion of the urinary tract of the patient, the elongate member having a distal retention member, a proximal retention member, and a medial portion disposed between the distal retention member and the proximal retention member,
the distal retention member configured to help retain at least a portion of the elongate member within a kidney of the patient, the distal retention member being formed of a non-dissolving material and being devoid of a dissolving material, the proximal retention member configured to help retain at least a portion of the elongate member within a bladder of the patient, the proximal retention member of the elongate member including a dissolving portion configured to dissolve in response to being exposed to a bodily fluid of the urinary tract for a period of time, the dissolving portion of the proximal retention member being disposed inside of a non-dissolving portion of the proximal retention member that is stable in the bodily fluid of the urinary tract of the patient, the dissolving portion having an inner surface defining at least a portion of the lumen, the dissolving portion having an inner diameter equal to an inner diameter of the medial portion, the non-dissolving portion of the proximal retention member being softer than the medial portion of the elongate member.

12. The ureteral stent of claim 11, wherein the dissolving portion is sufficiently firm to facilitate placement of the ureteral stent within the urinary tract of the patient.

13. The ureteral stent of claim 11, wherein at least one of the dissolving portion of the proximal retention member or the non-dissolving portion of the proximal retention member includes at least a portion of the medial portion of the elongate member.

14. The ureteral stent of claim 11, wherein the dissolving portion of the proximal retention member of the elongate member includes pores to facilitate dissolution of the dissolving portion.

15. The ureteral stent of claim 11, wherein the non-dissolving portion of the proximal retention member is sized to minimize irritation of the intramural tunnel when the dissolving portion of the proximal retention member has dissolved.

16. The ureteral stent of claim 11, wherein the dissolving portion of the proximal retention member dissolves before the non-dissolving portion of the proximal retention member is retrieved.

17. The ureteral stent of claim 11, wherein the non-dissolving portion of the proximal retention member has a shape before the period of time and the shape after the period of time.

18. A ureteral stent, comprising:

an elongate member configured to be disposed within a urinary tract of a patient, the elongate member defining a lumen configured to convey urine from a first portion of the urinary tract of the patient to a second portion of the urinary tract of the patient, the elongate member having a kidney retention member configured to help retain a portion of the elongate member within a kidney of the patient, the kidney retention member being configured to be substantially stable in response to being exposed to a bodily fluid and being devoid of a dissolving material, the elongate member having a bladder retention member configured to help retain a portion of the elongate member within a bladder of the patient, the bladder retention member having an inner portion configured to dissolve in response to being exposed to the bodily fluid for a period of time and an outer portion disposed outside of the inner portion, the outer portion defining at least one opening in a side wall of the outer portion, the at least one opening being fluidically isolated from the lumen before the period of time and being in fluid communication with the lumen after the period of time, the outer portion having a shape before the period of time and having the shape after the period of time.

19. The ureteral stent of claim 18, wherein the elongate member includes a medial portion disposed between the bladder retention member and the kidney retention member, at least a portion of the medial portion is constructed of a material that is substantially stable in the bodily fluid of the urinary tract of the patient.

* * * * *